United States Patent
Elssner et al.

(10) Patent No.: US 6,379,936 B1
(45) Date of Patent: Apr. 30, 2002

(54) COENZYMES USEFUL FOR THE SYNTHESIS OF L-CARNITINE

(75) Inventors: Thomas Elssner, Leipzig; Hans-Peter Kleber, Grossdeuben, both of (DE)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 09/992,005

(22) Filed: Nov. 26, 2001

Related U.S. Application Data

(62) Division of application No. 09/832,063, filed on Apr. 11, 2001, which is a division of application No. 09/582,440, filed as application No. PCT/IT99/00339 on Oct. 22, 1999, now abandoned.

(30) Foreign Application Priority Data

Oct. 27, 1998 (DE) .......................... 198 50 433
Oct. 27, 1998 (DE) .......................... 198 50 426

(51) Int. Cl.$^7$ .......................... C12P 13/00; C12N 9/88
(52) U.S. Cl. .......................... 435/128; 435/232
(58) Field of Search .......................... 435/128, 232

(56) References Cited

U.S. PATENT DOCUMENTS

| | | |
|---|---|---|
| 4,371,618 A | 2/1983 | Cavazza |
| 4,906,568 A | 3/1990 | Jung et al. |
| 5,028,538 A | 7/1991 | Seim et al. |
| 5,300,430 A | 4/1994 | Shapiro et al. |

FOREIGN PATENT DOCUMENTS

| | | |
|---|---|---|
| DE | 44 02 127 A | 7/1995 |
| FR | 2 715 167 A | 7/1995 |
| WO | 95 10613 A | 4/1995 |

OTHER PUBLICATIONS

Jung et al, Purification and properties of carnitine dehydratase from *Escherichia coli*—a new enzyme of carnitine metabolissm (1989) BBA. vol. 1003, pp. 270–276.

Etchler et al Cloning nucleotid sequence, and expression of the *Escherichia coli* gene encoding carnitine dehydratase (1994) J. of Bactiology, vol. 176, No. 10, pp. 2970–2975.

Zimmerman et al, Biotransformation in the production of L–carnitine (1997) In Chirality Ind. 11, pp. 287–305, ed. Collins et al, Wiley Chicchester, U.K.

*Primary Examiner*—Jon P. Weber
*Assistant Examiner*—Harry J Guttman
(74) *Attorney, Agent, or Firm*—Nixon & Vanderhye

(57) ABSTRACT

The invention described herein relates to coenzymes useful for the synthesis of L-carnitine, particularly a compound of coenzyme A, and more particularly gamma-butyrobetainyl-coenzyme A and crotonobetainyl-coenzyme A, to procedures for their preparation and to their use for the production of L(−)-carnitine from crotonobetaine and D(−)-carnitine.

2 Claims, No Drawings

COENZYMES USEFUL FOR THE SYNTHESIS OF L-CARNITINE

This application is a division of application Ser. No. 09/832,063, filed Apr. 11, 2001 now U.S. Pat. No. 6,337,197 which is a division of Ser. No. 09/582,440 filed Oct. 20, 2000, now abandoned the entire content of which is hereby incorporated by reference in this application, which is a 371 of PCT/IT99/00339 filed on Oct. 22, 1999.

The invention described herein relates to enzymes useful for the synthesis of L-carnitine, particularly a compound of coenzyme A, and more particularly gamma-butyrobetainyl-coenzyme A and crotonobetainyl-coenzyme A, to procedures for their preparation and to their use for the production of L(−)-carnitine from crotonobetaine and D(−)-carnitine.

To date we have no knowledge of isolated enzymes which are useful for the synthesis of L-carnitine, and in particular neither gamma-butyrobetainyl-coenzyme A nor crotonobetainyl-coenzyme A are known substances. When the abilities of these compounds to be used in the L(−)-carnitine production process are verified, the known technique and the knowledge relating to L(−)-carnitine production processes must be taken into consideration. Numerous chemical and biochemical or biotechnological processes are known for obtaining L(−)-carnitine. Most of the chemical synthesis processes yield D,L-carnitine as the result, by reaction of the racemic mixture with optically active separation acids, for example with optical isomers of tartaric acid, camphoric acid or camphorsulphonic acid, and via subsequent fractionated crystallization it is possible to obtain the L-carnitine enantiomer (for example, patents granted DD 23 217; DD 93 347; and published application DE 2997 672). All the synthesis processes to date present the disadvantage that D(+)-carnitine results as a discard product and must be disposed of and that only a maximum of 50% of the synthesized product is obtained as L(−)-carnitine. The therapeutic use of D,L-carnitine is non-substitutable, in that D(+)-carnitine is not substitutable, inasmuch as D(+)-carnitine is not only ineffective as regards the oxidation of fatty acids, but is also more competitive as a substance inhibiting the various transport systems and specific enzymes of L(−)-carnitine (Life Sciences 28[191] 2931–2938). For this reason, processes have been developed in recent years for stereospecific synthesis from initial achiral stages (for example, Tetrahedron, [1992], Vol. 48, 319–324).

Alternatives to the chemical synthesis of L(−)-carnitine are microbiological or enzymatic processes. In this way it proves possible to exploit the inverse reaction of L(−)-carnitine dehydrogenase (EC 1.1.1.108) to produce L(−)-carnitine from 3-dihydrocarnitine (U.S. Pat. No. 4,221,869). Being an NADH-dependent enzyme, the As preparation of reduction equivalents must be guaranteed. 3-Dihydrocarnitine, moreover, is very unstable. Various Entero-bacteriaceae strains are capable of transforming L(−)-carnitine into gamma-butyrobetaine via crotonobetaine in anaerobic conditions (patents granted DD 221 905, JP 6167 494, JP 61 234 794, JP 61 234 788). The metabolisation of L(−)-carnitine to crotonobetaine is reversible and is catalyzed by a stereospecific enzyme, L(−)-carnitine dehydratase (patents granted DD 281 735, DD 281,919). In this way, crotonobetaine can be used as the achiral end compound for the synthesis of L(−)-carnitine. A number of Proteus strains can also form L(−)-carnitine from crotonobetaine in aerobic conditions (U.S. Pat. No. 5,300,430). For the enzymatic synthesis of L(−)-carnitine from the discard product D(+)-carnitine, a racemate has been described (patent granted DD 300 181). A third possibility consists in obtaining L(−)-carnitine from gamma-butyrobetaine via gamma-butyrobetaine hydroxylase (EC/ 1.14.11.1) (publication DE 3123975). In patents EP 158 194, EP 195 944 and JP 61 199 793 processes are described based on the production of L(−)-carnitine from crotonobetaine or gamma-butyrobetaine by cultivating selected microorganisms on a supplementary source of C, for example glycinebetaine, in the presence of crotonobetaine or gamma-butyrobetaine.

L(−)-carnitine dehydratase (EC 4.2.1.89) catalyses the reversible transformation of crotonobetaine to L(−)-carnitine only in the presence of a low-molecular-weight factor F isolated from *Escherichia coli* and as yet unidentified (patent granted DD 281 735). From the immobilization of an L(−)-carnitine dehydratase isolated from the Entero-bacteriaceae family a process has been developed for the synthesis of L(−)-carnitine without the formation of sub-products (DD 281 910). The aforesaid low-molecular-weight factor F is equally indispensable for the racemization of D(+)- to L(−)-carnitine. The reduction of crotonobetaine to gamma-butyrobetaine also occurs only in the presence of this factor.

L(−)-carnitine (3-hydroxy-4-trimethylaminobutyrate) is a ubiquitous, naturally occurring compound. It is of fundamental importance as a carrier of acyl groups for the transport of long-chain fatty acids across the internal mitochondrial membrane. A3 a result of its central role in the metabolism of superior organisms, L(−)-carnitine is used in the therapy and prophylaxis of patients with various heart diseases as well as in the treatment of patients on dialysis (see: Pathology 17, [1985], 116–169). L(−)-carnitine supplementation is indispensable in the parenteral nutrition of neonates in the postnatal period and also in adults for longer periods (Gurtler and Löster, Carnitin [1996], 21–30). L-(−)-carnitine is a dietary supplement of growing importance.

The microbiological processes used for the synthesis of L(−)-carnitine present the disadvantage that the microorganisms, owing to their very limited number, may be poorly separated from their culture medium and new nutrient media must be made available continually for the cultivation. The result is that a substantial effort must be made to regenerate the evaporated L(−)-carnitine-containing culture fluid. In the synthesis of L(−)-carnitine from crotonobetaine in microbiological systems there is the possibility of transforming crotonobetaine to gamma-butyrobetaine via crotonobetaine reductase as a reaction competing with the synthesis reaction.

Of by no means secondary importance is the problem of using micro-organisms for the production of substances for pharmaceutical use. At times, the micro-organisms used come from pathogenic strains, or are highly engineered and contain extraneous genes, which is an aspect to which the Regulatory Authorities devote a great deal of attention.

The process for the enzymatic synthesis of L(−)-carnitine from crotonobetaine presents the disadvantage that a solution obtained from *E. coli* and devoid of proteins, through immobilized L(−)-carnitine dehydratase, must contain not only crotonobetaine, but also an unidentified factor F, which is essential for activation of the enzyme. Influences disturbing factor F produced by components of the protein-free solution cannot be excluded. The enzymatic synthesis of L(−)-carnitine can be optimized only to a limited extent, particularly in view of the fact that the amount of factor F used cannot be exactly quantified. The same factor F is of fundamental importance for the racemization of D(+)- to L(−)-carnitine described in *E. coli* Factor F cannot be replaced by known coenzymes or cofactors of enzymes (Jung et al., Biochim. Biophys. Acta. 1003 [1989] 270–276).

The cause of the disadvantages mentioned consists in our poor knowledge of the structure of factor F and of its role in activating the apoenzyme of L(−)-carnitine dehydratase. No other compounds are known which could stimulate activation of the apoenzyme of L(−)-carnitine dehydratase in the same way.

The purpose of the invention described herein is to make the stereospecific synthesis of L(−)-carnitine from crotonobetaine in an acellular medium enzymatically possible as well as the racemization of the discard product D(+)-carnitine to L(−)-carnitine. These enzymatically catalyzed reactions represent an alternative to the pure chemical synthesis of L(−)-carnitine or to the use of microbiological processes to obtain L(−)-carnitine.

The purpose of the invention is realizing the enzymatic synthesis of L(−)-carnitine from crotonobetaine with the above-mentioned gamma-butyrobetainyl-coenzyme A and L(−)-carnitine dehydratase without the formation of subproducts. It is also possible to realize the transformation of the physiologically ineffective discard product D(+)-carnitine to L(−)-carnitine using the system of the racemization of carnitine together with gamma-butyrobetainyl-coenzyme A.

Another purpose of the invention is realizing the enzymatic synthesis of L(−)-carnitine from crotonobetaine with crotonobetainyl-coenzyme A and L(−)-carnitine dehydratase without the formation of subproducts. It is also possible to realize the transformation of the physiologically ineffective discard product D(+)-carnitine to L(−)-carnitine using the system of the racemization of carnitine together with gamma-crotonobetainyl-coenzyme A.

The subject of the invention is a coenzyme A compound, hereinafter referred to as gamma-butyrobetainyl-coenzyme A, or crotonobetainyl-coenzyme A, respectively, which is capable of activating L(−)-carnitine dehydratase as a cofactor, in such a way that a reversible transformation of crotonobetaine to L(−)-carnitine may take place. The cofactor is also strictly necessary for the racemization of D(+)- to L(−)-carnitine as well as for the transformation of crotonobetaine to gamma-butyrobetaine. The subject of the invention described herein is a process for the synthesis and use of gamma-butyrobetainyl-coenzyme A as; well as the coenzyme itself.

The use of L(−)-carnitine dehydratase in combination with gamma-butyrobetainyl-coenzyme A or, alternatively with crotono-betainyl-coenzyme A, offers a new possibility of synthesis of L(−)-carnitine from crotonobetaine. From the simultaneous immobilization of L(−)-carnitine dehydratase and gamma-butyrobetainyl-coenzyme A, or, alternatively, crotonobetainyl-coenzyme A, an alternative to the industrial processes known to date for the production of L(−)-carnitine is developed. Similarly, the racemization system is used together with gamma-butyrobetainyl- coenzyme A, or with crotonobetainyl-coenzyme A, as a process for the synthesis of L(−)-carnitine from D(+)-carnitine.

According to the invention described herein, it is possible to synthesize L(−)-carnitine from crotonobetaine by means of L(−)-carnitine dehydratase (EC 4.2.1.89). For activation of the apoenzyme of L(−)-carnitine dehydratase only catalytic quantities of gamma-butyrobetainyl-coenzyme A, or crotonobetainyl-coenzyme A are necessary.

The condition for the synthesis of gamma-butyrobetainyl-coenzyme A is that gamma-butyrobetaine must be activated. Dried gamma-butyrobetaine hydrochloride is preferably used as the end product. The gamma-butyrobetaine hydrochloride is reacted with phosphorus trichloride at 15–70° C. (preferably at 250° C.) in an oxygen atmosphere. The gamma-butyrobetainyl chloride formed is separated from further products and end substances by bubbling with nitrogen.

The gamma-butyrobetainyl chloride thus obtained is suitable for the synthesis of gamma-butyrobetainyl-coenzyme A. Coenzyme A is first suspended in an iced mixture of 1M of sodium bicarbonate at pH 7.5–9.5 (preferably pH 8.5). To this is added a definite amount of gamma-butyrobetainyl chloride (preferably in excess) keeping the pH values under control. After 15–30 minutes the reaction is complete. The formation of gamma-butyrobetainyl-coenzyme A is checked by HPLC (Spherisorb, $C_{18}$ column) and finally subjected to a further purification stage (ion-exchange chromatography on DOWEX 50). The purity is checked again by HPLC (Spherisorb, $C_{18}$ column). The physicochemical properties were determined on the washed product (see following table).

| Property | Gamma-butyrobetainyl-coenzyme A |
| --- | --- |
| Molar mass | 895.2 |
| Maximum absorption | 206 nm, 258 nm |
| Molar extinction coefficient ($\epsilon_{260}$) | 16.11 mmol$^{-1}$ cm$^{-1}$ |
| pH stability for 1 h | 3–10 |
| Temperature stability (1 h) | 100%: −20° C. |
| | >90%: 0° C. to 90° C. |
| Solubility | water |

For the L(−)-carnitine dehydratase activation test according to the invention purified gamma-butyrobetainyl-coenzyme A is supplied (preferably 1–10 nmol) on potassium phosphate buffer (10 mM pH 7.5), which is added with partly concentrated L(−)-carnitine dehydratase (without factor F showing any activity) and the crotonobetaine solution to be metabolized (1 M) and incubated at 37° C.

The L(−)-carnitine formed was subsequently tested with an optical test with the aid of carnitine acetyltransferase (according to BERGMEYER (1970)). A similar procedure was adopted in the racemization reaction test, in which a solution of D(+)-carnitine (1 M) was added in the place of crotonobetaine. The L(−)-carnitine formed can be determined exactly by prior testing of the system with known solutions of L(−)-carnitine.

For testing the activation of the enzymatic system according to the invention described herein, which transforms crotonobetaine to gamma-butyrobetaine, purified gamma-butyrobetainyl-coenzyme A is supplied (preferably 1–10 nmol) on a temperate potassium phosphate buffer (preferably 37° C.) and bubbled with nitrogen (50 mM, at pH 7.8), and the crotonobetaine enzymatic reduction system is added (without factor F showing any attivity) as well as dithionite (preferably 50 mM) and benzyl-viologen (preferably 1 mM). After addition of the crotonobetaine solution to be metabolized (3.75 M) the gamma-butyrobetaine formed can be tested using the oxidized-benzyl-viologen-based optical test.

Similarly, the condition for the synthesis of crotonobetainyl-coenzyme A is that gamma-butyrobetaine be activated. Dried gamma-butyrobetaine hydrochloride is preferably used as the end product. The gamma-butyrobetaine hydrochloride is reacted with phosphorus trichloride at 15–70° C. (preferably at 25° C.) in an oxygen atmosphere. The crotonobetainyl chloride formed is separated from further products and end substances by bubbling with nitrogen.

The crotonobetainyl chloride thus obtained is suitable for the synthesis of crotonobetainyl-coenzyme A. Coenzyme A is first suspended in an iced mixture of 1M of sodium bicarbonate at pH 7.5–9.5 (preferably pH 8.5). To this is added a definite amount of crotonobetainyl chloride (preferably in excess) keeping the pH values under control. After 15–30 minutes the reaction is complete. The formation of crotonobetainyl-coenzyme A is checked by HPLC (Spherisorb, $C_{18}$ column) and finally subjected to a further purification stage (ion-exchange chromatography on DOWEX 50). The purity is checked again by HPLC (Spherisorb, $C_{18}$ column). The physicochemical properties were determined on the washed product (see following table).

| Property | Crotonobetainyl-coenzyme A |
| --- | --- |
| Molar mass | 893.6 |
| Maximum absorption | 208 nm, 260 nm |
| Molar extinction coefficient ($\epsilon_{260}$) | 20.21 mmol$^{-1}$ cm$^{-1}$ |
| pH stability for 1 h | 2–10 |
| Temperature stability (1 h) | 100%: -20° C. to 0° C. |
|  | 75%: 20° C. to 60° C. |
| Solubility | water |

For the L(−)-carnitine dehydratase activation test according to A the invention purified crotonobetainyl-coenzyme A is supplied (preferably 1–10 nmol) on potassium phosphate buffer (10 mM pH 7.5), which is added with partly concentrated L(−)-carnitine dehydratase (without factor F showing any activity) and the crotonobetaine solution to be metabolized (1 M) and incubated at 37° C.

The L(−)-carnitine formed was subsequently tested with an optical test with the aid of carnitine acetyltransferase (according to BERGMEYER (1970)). A similar procedure was adopted in the racemization reaction test, in which a solution of D(+)-carnitine (1 M) was added in the place of crotonobetaine. The L(−)-carnitine formed can be determined exactly by prior testing of the system with known solutions of L(−)-carnitine.

For testing the activation of the enzymatic system according to the invention described herein, which transforms crotonobetaine to gamma-butyrobetaine, purified crotonobetainyl-coenzyme A is supplied (preferably 1–10 nmol) on a temperate potassium phosphate buffer (preferably 37° C.) and bubbled with nitrogen (50 mM, at pH 7.8), and the crotonobetaine enzymatic reduction system is added (without factor F showing any attivity) as well as dithionite (preferably 50 mM) and benzyl-viologen (preferably 1 mM). After addition of the crotonobetaine solution to be metabolized (3.75 M) the gamma-butyrobetaine formed can be tested using the oxidized-benzyl-viologen-based optical test.

EXAMPLE 1

Formation of L(−)-carnitine from crotonobetaine by means of concentrated L(−)-carnitine dehydratase and gamma-butyrobetainyl-coenzyme A (BB-CoA) after 10 minutes' incubation at 37° C. on potassium phosphate buffer (10 mM, pH 7.5).

| L-carnitine dehydratase ($\mu$g) | BB-CoA ($\mu$mol) | Crotonobetaine ($\mu$mol) | Carnitine synthesis ($\mu$mol) |
| --- | --- | --- | --- |
| 10 | 0.002 | 20 | 0.18 |
| 10 | 0.002 | 0 | 0 |
| 10 | 0 | 20 | 0 |
| 0 | 0.002 | 20 | 0 |

EXAMPLE 2

Formation of L(−)-carnitine from D(+)-carnitine by means of a system of racemization of carnitine and gamma-butyrobetainyl-coenzyme A (BB-CoA) after 10 minutes' incubation at 37° C. on potassium phosphate buffer (10 mM, pH 7.5).

| Carnitine racemization system ($\mu$g) | BB-CoA ($\mu$mol) | Crotonobetaine ($\mu$mol) | Carnitine synthesis ($\mu$mol) |
| --- | --- | --- | --- |
| 30 | 0.002 | 20 | 0.162 |
| 30 | 0.002 | 0 | 0 |
| 30 | 0 | 20 | 0 |
| 0 | 0.002 | 20 | 0 |

EXAMPLE 3

Formation of L(−)-carnitine from crotonobetaine by means of concentrated L(−)-carnitine dehydratase and crotonobetainyl-coenzyme A (CB-CoA) after 10 minutes' incubation at 37° C. on potassium phosphate buffer (10 mM, pH 7.5).

| L-carnitine dehydratase ($\mu$g) | CB-CoA ($\mu$mol) | Crotonobetaine ($\mu$mol) | Carnitine synthesis ($\mu$mol) |
| --- | --- | --- | --- |
| 10 | 0.002 | 20 | 0.271 |
| 10 | 0.002 | 0 | 0 |
| 10 | 0 | 20 | 0 |
| 0 | 0.002 | 20 | 0 |

EXAMPLE 4

Formation of L(−)-carnitine from D(+)-carnitine via a system of racemization of carnitine and crotonobetainyl-coenzyme A (CB-CoA) after 10 minutes' incubation at 37° C. on potassium phosphate buffer (10 mM, pH 7.5).

| Carnitine racemization system ($\mu$g) | CB-CoA ($\mu$mol) | Crotonobetaine ($\mu$mol) | Carnitine synthesis ($\mu$mol) |
| --- | --- | --- | --- |
| 30 | 0.002 | 20 | 0.243 |
| 30 | 0.002 | 0 | 0 |
| 30 | 0 | 20 | 0 |
| 0 | 0.002 | 20 | 0 |

What is claimed is:

1. An enzymatic process for the stereospecific synthesis of L(−)-carnitine comprising the steps of:
    (a) in an acellular medium bringing crotonobetainyl-coenzyme A and. L(−)-carnitine dehydratase (EC 4.2.1.89) into contact with each other, then
    (b) adding D(+)-carnitine to the medium of step (a) to enzymatically convert the D(+)-carnitine to L(−)-carnitine, and thereafter
    (c) isolating the L(−)-carnitine so produced.

2. An enzymatic process for the stereospecific synthesis of L(−)-carnitine comprising the steps of:
    (a) in an acellular medium bringing crotonobetainyl-coenzyme A and L(−)-carnitine dehydratase (EC 4.2.1.89) into contact with each other, then
    (b) adding crotonobetaine to the medium of step (a) to enzymatically convert the crotonobetaine to L(−)-carnitine, and thereafter
    (c) isolating the L(−)-carnitine so produced.

* * * * *